United States Patent [19]

Riuli et al.

[11] 4,338,267
[45] Jul. 6, 1982

[54] MEDICAL GAS HUMIDIFIER WITH AUDIBLE PRESSURE RELIEF VALVE AND METHOD OF USE

[75] Inventors: Arduino E. Riuli, Wayne, N.J.; Robert W. Anastasia, Flushing, N.Y.; Bernard F. Kopacz, Little Falls, N.J.

[73] Assignee: Becton, Dickinson and Company, Paramus, N.J.

[21] Appl. No.: 207,502

[22] Filed: Nov. 17, 1980

Related U.S. Application Data

[63] Continuation of Ser. No. 69,037, Aug. 23, 1979, abandoned, which is a continuation-in-part of Ser. No. 820,628, Aug. 1, 1977, abandoned.

[51] Int. Cl.³ .............................................. A61M 11/06
[52] U.S. Cl. ........................... 261/121 R; 128/200.11; 128/200.13; 128/202.22; 261/DIG. 65
[58] Field of Search ...................... 261/121, DIG. 65; 128/186–194, 200.11, 200.12, 200.13, 202.22; 137/469, 557; 116/70; 251/338

[56] References Cited

U.S. PATENT DOCUMENTS

| | | | |
|---|---|---|---|
| 1,209,182 | 12/1916 | Miller | 251/338 |
| 1,493,570 | 5/1924 | Slate | 116/70 |
| 2,104,934 | 1/1938 | Smith | 251/338 |
| 2,902,269 | 9/1959 | Eichelman | 261/DIG. 65 |
| 3,459,218 | 8/1969 | Cranage | 137/557 |
| 3,572,660 | 3/1971 | Mahon | 261/DIG. 65 |
| 3,610,276 | 10/1971 | Seelman | 137/469 |
| 3,611,981 | 10/1971 | Warncke | 137/557 |
| 3,807,445 | 4/1974 | McPhee | 261/DIG. 65 |
| 4,011,288 | 3/1977 | Assenheimer et al. | 261/DIG. 65 |
| 4,039,639 | 8/1977 | Kankel et al. | 261/DIG. 65 |

Primary Examiner—Gregory N. Clements
Attorney, Agent, or Firm—Richard J. Rodrick

[57] ABSTRACT

The disclosure is of an improved method and apparatus for humidifying medical gases. The apparatus improved is of the type which comprises a portable housing enclosing a water reservoir, a gas chamber, gas inlet and outlet conduits to carry the gas through the water reservoir and gas chamber. The improvement comprises an audible pressure relief valve in association with the gas chamber. When a predetermined pressure within the gas chamber has been exceeded, the pressure relief valve opens to relieve the excess pressure and to simultaneously warn the operator than the predetermined pressure level has been exceeded. The alerted operator may then check to determine if there has been a malfunction in the apparatus or ancillary apparatus.

9 Claims, 7 Drawing Figures

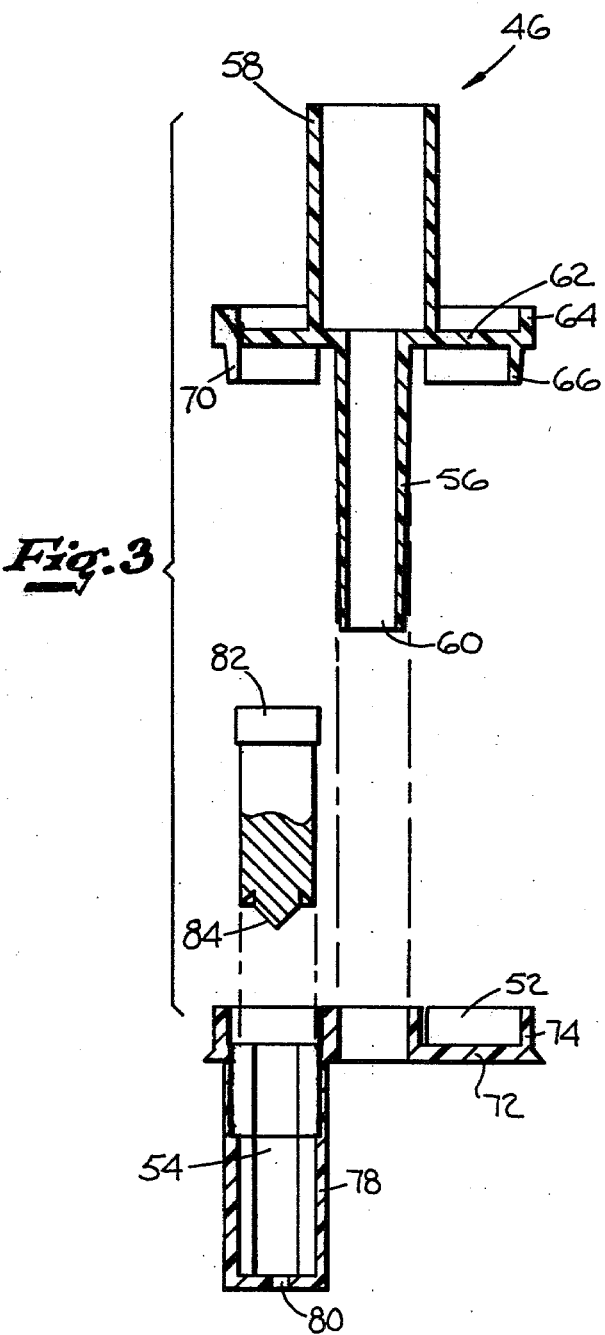
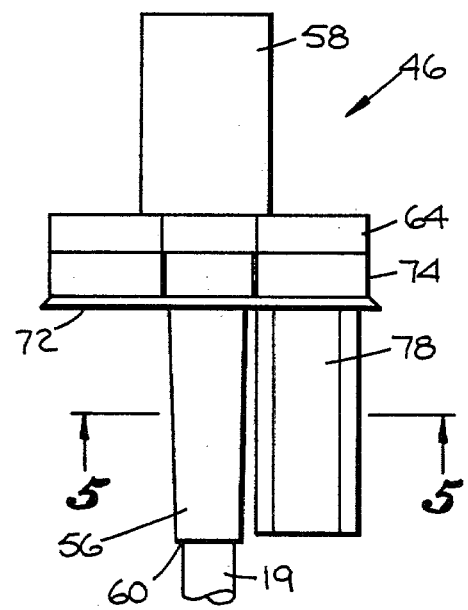
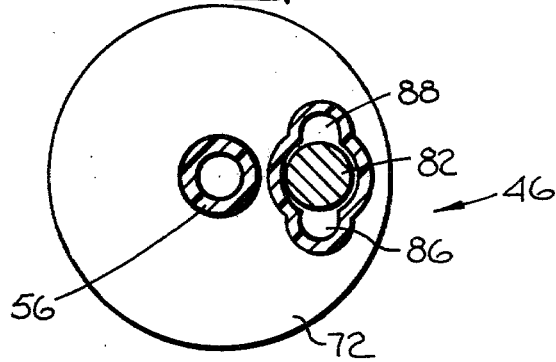

MEDICAL GAS HUMIDIFIER WITH AUDIBLE PRESSURE RELIEF VALVE AND METHOD OF USE

CROSS REFERENCE TO RELATED APPLICATION

This is a continuation, of application Ser. No. 69,037, filed 8/23/79, abandoned, which application is a continuation-in-part application of Ser. No. 820,628, filed Aug. 1, 1977, abandoned.

BACKGROUND OF THE INVENTION

1. Field of the Invention

The invention concerns methods, devices and apparatus for moisturizing medical gases prior to their administration to a mammal, including a human in need of such treatment.

2. Brief Description of the Prior Art

The treatment of very ill, hospitalized patients with a variety of medical gases including oxygen has been found invaluable in a variety of medical disabilities. Generally, these medical gases as provided by the manufacturer are relatively dry and tend to dry mucous membranes of the treated patient unless humidified prior to administration. Medical gas mositurizers are generally well known. Representative of such moisturizers are those described in U.S. Pat. Nos. 3,793,810 and 3,836,079. These moisturizers are generally associated with the patient undergoing treatment through flexible tubing means which delivers the humidified gas to the patient. Those skilled in the art have appreciated that on occasion an agitated or uncomprehending patient may cause a partial or complete occlusion of the flexible tubing, thereby creating an undesirable back-pressure in the moisturizers and interrupting therapy. In such instances, it is highly important that attending medical personnel be alerted to (1) the fact of occlusion or other cause of back-pressure in the moisturizer and (2) the severity of the occlusion. Given the locality of the treatment (generally a hospital or like facility) it is also important that the means of alerting the personnel be positive, readily recognized and located as to site of the problem, non-irritating to other patients and not distracting to personnel not authorized to respond. It is also important that the alert means not be a means of agitating the patient being treated.

The method and apparatus of our invention is an improvement over prior art mositurizing apparatus, solving the above-described problems of the prior art and meeting the requirements described above for alerting medical personnel should a back-pressure problem develop.

Audible pressure relief valves are also generally well known; see for example U.S. Pat. Nos. 777,538; 1,493,570; and 3,459,218.

SUMMARY OF THE INVENTION

The invention comprises, in an apparatus for moisturizing medical gases and which comprises, (a) a portable housing having an upper and a lower portion; (b) a reservoir chamber within the lower portion of said housing adapted for holding a column of water and having an upper and a lower zone; (c) a gas chamber within the upper portion of said housing and in gas communication with said reservoir chamber; (d) a first passage communicating between the lower zone of said reservoir chamber and the outside of said housing; and (e) a second passage communicating between said gas chamber and the outside of said housing; the improvement, which comprises; (1) a whistle section attached to said housing; (2) a decompression chamber communicating with said whistle; and (3) valve means between said decompression chamber and said gas chamber, said valve means being adapted to open fluid communication between said decompression chamber and said gas chamber in response to a predetermined gas pressure in said gas chamber, said valve means closing said fluid communication when less than said predetermined gas pressure is in said gas chamber.

The term "moisturizing" as used throughout the specification and claims means raising the water vapor content of a given medical gas. Moisturizing of medical gases is commonly carried out prior to administration of the gas to a mammal so as to not dry out mucous membranes in mammals undergoing medical gas therapy.

The improved apparatus of the invention provides an intermittent, low frequency, non-irritating audible warning to the technician operator that a predetermined pressure in the gas chamber has been exceeded. The operator being so warned, may then check the humidifying apparatus and ancilliary equipment to determine the cause of pressure build up for the purpose of taking corrective measures.

The invention also comprises a method of administering humidified medical gases to a mammal in need of such therapy, employing the apparatus of the invention. The method comprises providing the above-described apparatus, including water in the reservoir chamber; introducing a medical gas into the first passage whereby it passes through the water in the reservoir chamber and out of the second passage; attaching conduit means to the outside of the second passage; attaching gas administration means to conduit means; associating the administration means with said mammal and administering the moisturized medical gas to the mammal therethrough.

BRIEF DESCRIPTION OF THE DRAWINGS

FIG. 3 is a cross-sectional side elevation of the valve means, decompression chamber and whistle components of the apparatus shown in FIG. 1, but disassembled.

FIG. 4 is an isometric view of the components seen in FIG. 3, but assembled together.

FIG. 5 is a view along lines 5—5 of FIG. 4.

DETAILED DESCRIPTION OF THE INVENTION

A complete understanding of the invention may be conveniently obtained by reference to the accompanying drawings of FIGS. 1-7, inclusive.

Figure 1:
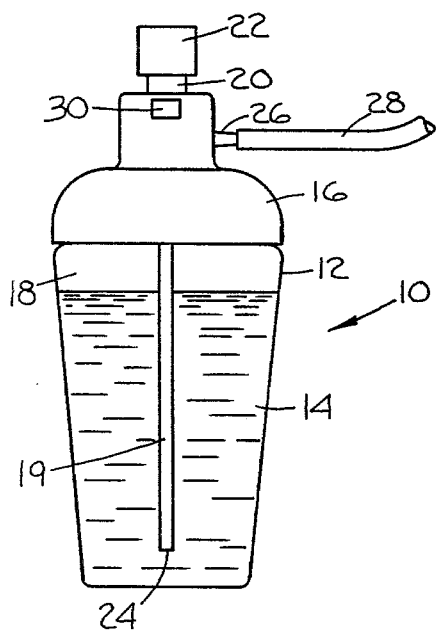
FIG. 1 is an isometric view of an embodiment apparatus of the invention.

FIG. 1 is an isometric view of the embodiment apparatus of the invention. Apparatus 10 comprises a jar 12 adapted to contain a column of water 14. The jar 12 with a closure cap 16 comprises a housing to define a gas chamber 18 above the column of water 14. A gas inlet conduit 19 has a first end connected to nipple 20.

Nipple 20 is an integrally molded part of cap 16 and is adapted to be coupled by nut 22 to a tubular carrier for a source of medical gases. Conduit 19 has a terminal end 24 beneath the surface of water 14. A gas outlet conduit 26 originates in gas chamber 18 and terminates outside of apparatus 10. As shown in FIG. 1, gas outlet conduit 26 is attachable to a tubular carrier 28 for transmitting the moisturized gas to the point of its use. Piercing cap 16 is an exhaust portal 30 which functions as part of a pressure relief valve system and is part of a whistle as will be described in greater detail hereinafter.

In operation, the apparatus 10 is connected by coupling nut 22 to a metered flow of a medical gas. The medical gas, such as for example oxygen, is carried from its source to nipple 20 and by its connection to conduit 19. Conduit 19 carries the oxygen to the bottom of water column 14 and discharges the oxygen therein through terminal end 24. The resulting gas bubbles generally form a spheroid shape as they ascent through the water column 14. During ascent, the medical gas increases its content of water vapor. Upon moisturization, the medical gas is released into gas chamber 18. Under normal conditions, the moisturized medical gas is discharged to outlet conduit 26 and conducted to the point where it is required, for example, administered to a mammal requiring gas therapy through the tube 28 and appropriate administrative means. Under normally employed flow conditions, gas pressure in gas chamber 18 is less than about 2 psig, the rate of oxygen flow into apparatus 10 being about equal to the rate of flow out of apparatus 10. If the outflow is obstructed, for example by an accidental crimping of the tubular carrier 28, there may be an increase of gas pressure in gas chamber 18 as inflowing gas accumulates. This is a potential hazard which can damage the apparatus and interrupt gas therapy of the mammal undergoing treatment. In the apparatus 10 of the invention, a means is provided for the relief of excess pressure to exhaust port 30 with a simultaneous audible warning signal to alert personnel to the situation.

Figure 2:
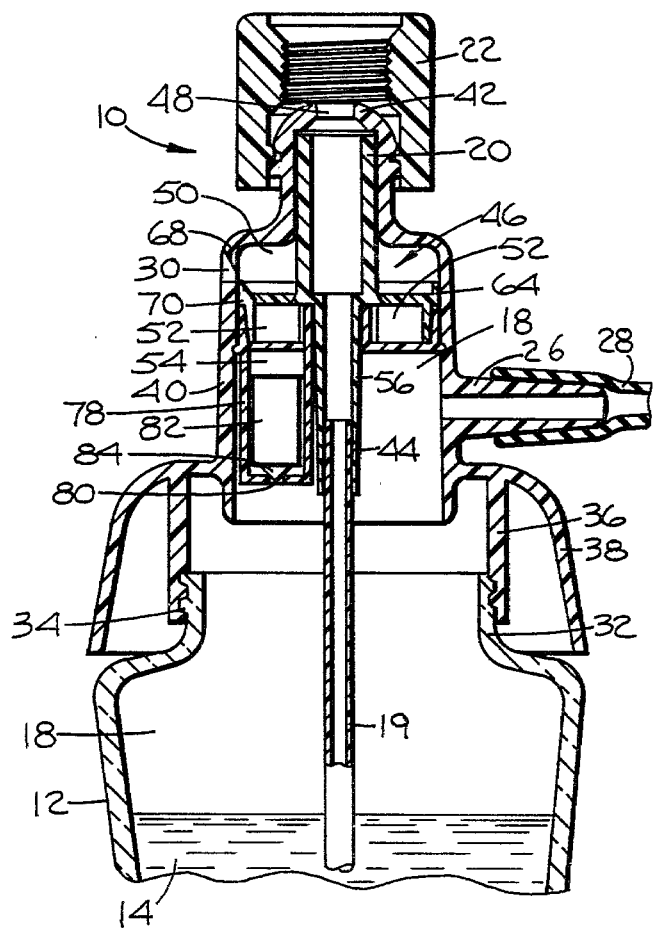
FIG. 2 is a cross-sectional side elevation in part of the apparatus shown in FIG. 1.
Figure 6:
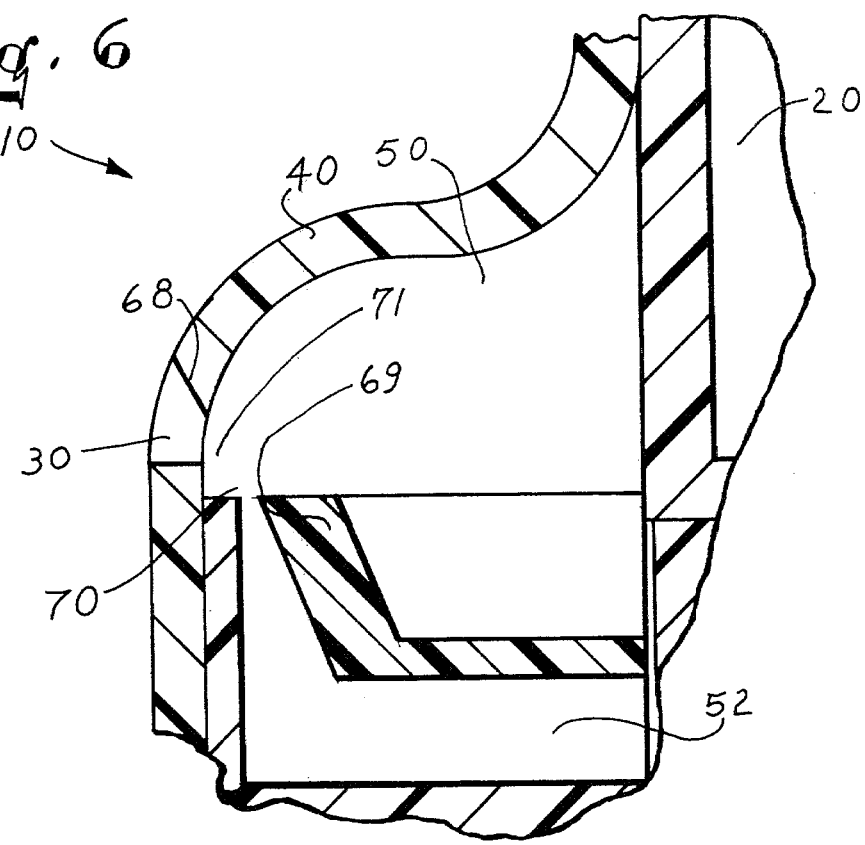
FIG. 6 is an exploded view of the whistle portion shown in FIG. 2.

Referring now to FIG. 2, a cross-sectional side elevation in part of the apparatus 10, further details will be observed. The jar 12 has a neck 32 adapted by threads 34 for engagement with cap 16. The cap 16 has a structural shoulder 36 adapted to secure cap 16 to jar 12. A skirt portion 38 of cap 16 protects the attachment of cap 16 to jar 12. The mid portion of cap 16 comprises sidewalls 40 which terminate at the opposite end in the formation of nipple 42. Nipple 42 is adapted to be coupled by coupling nut 22 to a tubular nipple associated with a source of medical gases. The interior cavity defined by the nipple 42, walls 40 and shoulder 36 is an extension of the gas chamber 18 above water 14. As seen in FIG. 2, gas chamber 18 communicates to the exterior of apparatus 10 by gas outlet conduit 26. Traversing the gas chamber 18 is conduit 19, the first end 44 of which is in closed communication with nipple 42 to intermediary insert 46. Insert 46 may be more clearly seen in FIG. 4 which is an isometric view of the components seen in FIG. 3 but assembled. More specifically, the insert 46 comprises a means for joining conduit 19 to the inlet orifice 48 of nipple 42 so that medical gases conducted to nipple 42 are carried by conduit 19 to the bottom of water column 14. The insert 46 also provides a means for dividing gas chamber 18 into a whistle or resonating chamber 50, a decompression chamber 52 and a pressure chamber 54.

Referring now to FIG. 3, insert 46 may be observed in a disassembled condition. Insert 46 comprises a tubular member 56 having a first end 58 adapted to mate with nipple 42 to provide a gastight hermetic seal therewith. The lower end 60 of tubular member 56 is of reduced diameter and is adapted to sealingly engage the first end 44 of conduit 19 in a gastight hermetic seal. Radially disposed about the mid-section of tubular member 56 and integrally molded therewith is a wall 62 having an upper flange 64 and a lower flange 66. Upper flange 64 as seen best in FIG. 2, frictionally engages the inside of cap 16 wall 40 so that the wall 62 together with the inside of wall 40 forms an annular resonating or whistle chamber 50. In other words, the wall 62 together with a portion of the inside of walls 40 of cap 16 form a whistle bell. Referring to the exploded view in FIG. 6, it is seen that the resonating chamber 50 communicates with the exterior through exhaust portal 30. The exhaust portal 30 has the shape of a notch in wall 40 (see FIG. 6). The throat of the "V" shaped notch is a whistle aperture and the upwardly extending margin of the notch provides a whistle lip or reed 68. Gas is supplied to the whistle aperture from the decompression chamber 52 which is an annular chamber disposed about the periphery of insert 46 and having a channel 70 communicating between decompression chamber 52 and exhaust portal 30. In the preferred embodiments, the reed 68 is disposed at an angle of 30° to the sidewall 40. Air directed to the aperture 30 and at reed 68 is preferably deflected by one-half the reed 68 angle, i.e.; 15° by deflector 69. The nozzle 71 therefore has an angle splitting the reed 68 angle to provide a sharp, crisp, whistle even at low pressures.

Referring again to FIG. 3, it is seen that decompression chamber 52 is formed by the annular, dish-shaped member 72 whose outer flange 74 forms a frictional fit between flange 66 of wall 62 and the inner wall of cap 16. Thus, decompression chamber 52 is formed by flanges 66 and 74 with walls 62 and 72. The decompression chamber 52 communicates through channel 70 to exhaust portal 30 (see FIG. 2). The decompression chamber 52 also communicates with pressure chamber 54 on its lower side. Pressure chamber 54 is defined by valve casing 78 which has valve opening 80 in its lower surface. Slidably mounted in valve casing 78 is valve member 82 which has a tapered end 84. Tapered end 84 is adapted to mate with and close valve opening 80 when valve member 82 is in the lower position within valve casing 78. In the lower position, member 82 closes valve opening 80 thereby interrupting communication between gas chamber 18 and decompression chamber 52 (see FIG. 2).

FIG. 4 is an isometric view of the assembled components shown in FIG. 3, and shows the assmebled insert 46.

Referring now to FIG. 5, a view along lines 5—5 of FIG. 4, the valve member 82 can be seen slidably mounted within the pressure chamber 54.

A necessary structure in the improved apparatus of the invention resides in a channel bypass around the poppet weight which comprises the valve member 82. This channel bypass communicates between the decompression chamber 52 and the valve orifice 80 when the poppet 82 is lifted out of its valve seat 80. The channel bypass may comprise relatively narrow channels (or flutes) 86, 88 (see FIG. 5). In other words the flutes 86 and 88 provide a gas by-pass for the communication between gas chamber 18 and decompression chamber 52 when valve member 82 moves upward to open valve opening 80. Valve member 82 is a gravity seated poppet which moves upward in pressure chamber 54 when the gas pressure in chamber 18 exceeds a predetermined level. The channel bypass of the excess gas around the poppet valve weight 82 to relatively narrow bypass conduits is an important structure which functions to make the poppet 82 more responsive over very low and narrow ranges of pressure changes. It is desirable that the valve member 82 be very quickly responsive to an increase in gas pressure in chamber 18 and be very sensitive to even slight increases in pressure so that the member 82 will open valve 80 frequently even at low flow rates in response to very slight pressure increases in chamber 18. This desirable attribute of member 82 may be obtained by constructing member 82 as small and light as possible. For example, if it is desired to maintain the pressure in chamber 18 between 0.5 and 2 psig (a relatively narrow range) valve member 82 having a weight of about 6 grams will function as desired provided it is constructed as hereinafter described more fully.

Figure 7:
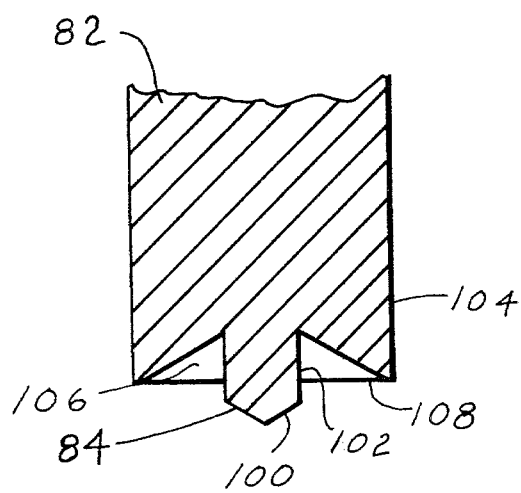
FIG. 7 is an exploded view of the lower portion of the poppet component shown in FIG. 3.

FIG. 7 is an exploded cross-sectional view of the lower end of valve member 82 including the tapered end 84 which mates with valve seat 80. The lower end of valve member 82 presents a plurality of surfaces upon which air or other gas passing through the valve will impinge and by its force lift or keep the valve member 82 from its engagement with valve seat 80. The first surface encountered by such gas is the cone shaped, convex surface 100 on the tapered end 84. Surface 100 leads from the lowermost point of end 84 upward at a 90° angle along surface 102 which is generally the surface of the side of a cylinder, offering relatively little resistance to the flow of gas. Between surface 102 and the cylindrical sidwalls 104 of the main body of valve member 82 is an annular concave recess, presenting a surface 106. The valve member 82 is lifted out of valve set 80 by underlying gas pressure, forcing against at least part of the surface 100. As the valve member 82 clears the valve seat 80, the force of the gas flow is then against the full area of surface 100. The force is also exerted against surface 102 and the surface 106. The escaping gas then passes over edge 108 before by-passing the member 82. This unique design optimizes the lift from the flowing gas and enables one to employ very small, light masses as the valve member 82. Initially a relatively high gas pressure is required to open the valve because only surface 100 is subject to a lifting force. Once valve member 82 is lifted, the gas pressure is relieved to some degree and valve member 82, in view of a reduced lifting force, ordinarily would be subject to resenting in valve seat 80 to close the valve, until gas pressure built up again, there would be intermittent opening and closing of the valve. However, because the added surface area 106 and the angular configuration of the surface add lifting surface, once the valve is open a lower gas pressure is required to maintain the valve member 82 lifted off the valve seat 80. This results in an uninterrupted gas flow until the lower limit of the desired pressure range is reached. One may thus maintain the valve open for intermittent periods over very narrow and desired pressure ranges. The surface area for the surface 106 and its surface angle may be calculated for any given mass of member 82 by the following calculation.

Poppet Lift static lift (g = o)

Poppet Lift -continued $F_s = PA$ dynamic lift
$r_d = k \cdot g^2$
at incipient motion of poppet (t = o$^+$)

$F_d$ = Dynamic lift
$F_s$ = Static lift
A = Area of orifice
P = Pressure in Chamber or jar
G = Gravity Thus, it will be appreciated that the particular geometry called for by the embodiment of FIG. 7 provides the optimum control of the poppet weight, especially at low pressures. In operation, and initially, excess gas pressure is against the full surface area of surface 100 as shown in FIG. 7. Upon opening of the valve, the force is also exerted against the surface 102 and the surface 106. Escaping gas passes over the edge 108 before bypassing the member 82 as previously described. This unique design optimizes the lift from the flowing gas and enables one to employ very small, light members as the valve member 82. Initially, a relatively high gas pressure is required to open the valve because only surface 100 is subject to a lifting force. Once valve member 82 is lifted, the gas pressure is relieved to some degree and valve member 82, in view of the reduced lifting force, ordinarily would be subject to reseating in valve 80 to close the valve until gas pressure built up again. There will be an intermittent opening and closing of the valve. After the poppet unseats, the velocity of escaping gas propels the poppet upward by impinging on the unique face cavitation as described above. This velocity decays rapidly because of the unit configuration of the poppet face, allowing the poppet to recede before all the pressure is spent in the humidifier bottle. If the patient's oxygen supply tubing was totally occluded, a rapid poppeting would occur at an average flow rate of 5 to 8 liters per minute (of oxygen). If there is a partial occlusion of the patient's oxygen supply tube (or any other component of the circuit) the poppet would only relieve the pressure build-up in the circuit to a safe level. This of course is highly advantageous. As an example, consider the following. The maximum allowable pressure in a humidifier circuit is about 2 psig. The back pressure caused by frictional loss in the patient's supply tube and nasal cannula affect a 0.2 to 0.6 psig pressure in the humidifier bottle (functional). When the patient's supply tube or nasal cannula is partially occluded, the patent may be receiving 75% of the set flow rate (set rate 8 liters per minute, patient receives 6 liters per minute, 2 liters per minute increases pressure in bottle to critical pressure, i.e.; 2 psig). A velocity propelled poppet as employed in the embodiment of FIG. 7 will relieve the pressure down to approximately 1.2 psig and rapidly reset the poppet (non-sailing), thereby signalling the technicial of the problem. However, the apparatus continues to maintain essentially all of the flow which bypasses the occlusion (0.2 to 0.6 psig) required to maintain flow of oxygen to the patient. The frequency of the poppeting at a given flow rate will alert the technician to the degree of occulsion. This audible signal has also been observed to be essentially non-irritating and not distracting to the patient or other patients and non-concerned personnel. It also does not tend to excite the patient.

In summary, when there is an accumulation of gas in chamber 18, valve member 82 is forced upward to open valve opening 80. The excess gas rushes up flutes 86 and 88 and into the decompression chamber 52. The decompressed gas is channeled through channel 70 to ambience by way of exhaust portal 30 and the whistle aperture, creating as it does so in cooperation with whistle lip 68 and the resonating chamber 50 a resonating whistle of substantially constant pitch. As long as the gas pressure in chamber 18 remains excessive, gas will be released to the atmosphere as described above and the whistle continues. When pressure within gas chamber 18 falls to a level whereby member 82 falls in valve casing 78 to close opening 80, the flow of gas past the whistle lip and out of the portal 30 ceases so the whistle ceases. As the gas builds up again, the valve reopens and whistle begins again. In this manner, intermittent whistling is obtained until alerted personnel arrive to correct the condition causing the excessive gas build up.

It will be appreciated that whistling must be obtained promptly at relatively low pressures in the devices of the invention. A sharp, crisp whistle is obtained during operation of the devices of the invention even at low pressure because of the unique whistle structure previously described and employed in the preferred embodiment of the invention.

It will be readily apparent to those skilled in the art that many modifications can be made to the embodiments shown in the accompanying drawings without departing from the spirit of the invention. For example the whistle bell may be molded on the exterior of the cap 16 although it is preferably wholly contained within the cap structure.

We claim:

1. A method of administering a mositurized medical gas to a mammal in need of such therapy, which comprises:
providing apparatus for moisturizing medical gases and which comprises:
(a) a portable housing having an upper portion and a lower portion;
(b) a reservoir chamber within the lower portion of said housing adapted for holding a column of water and having an upper and a lower zone;
(8c) a gas chamber within the upper portion of said housing and in gas communication with said reservoir chamber;
(d) a first passage communicating between the lower zone of said reservoir chamber and the outside of said housing, said passage having a first open end in the lower zone of the reservoir chamber and a second open end on the outside of the housing and adapted for connection to a source of said medical gases whereby medical gases may be introduced into the reservoir chamber and moisturized by contact with water held therein;
(e) a second passage communicating between said gas chamber and the outside of said housing, said second passage having a first open end in said gas chamber and a second open end on the outside of said housing and adapted to connect with a means of delivering moisturized medical gases passed from said gas chamber to a patient in need of receiving said moisturized gases;
(f) a whistle attached to the upper portion of said housing, and which comprises a whistle reed, a nozzle directing gases toward the reed, and a resonating chamber;
(g) a decompression chamber communicating with said nozzle; and
(h) valve means between said decompression chamber and said gas chamber, said valve means comprising a valve casing, a valve seat in the bottom of said casing surrounding a valve orifice defining an inlet into the valve casing, said valve orifice opening into said gas chamber, a lightweight poppet adapted to seat in said valve seat under the force of gravity of close the valve orifice and to lift out of said valve seat under a predetermined pressure of gas exerted on the seated poppet through the orifice, and a plurality of relatively narrow bypass channels extending longitudinally through said casing and disposed around said poppet which communicate between said decompression chamber and said valve orifice as soon as said poppet is lifted out of said valve seat, said valve means being adapted to rapidly open fluid communication between said decompression chamber and said gas chamber in response to a predetermined gas pressure in said gas chamber, said valve means closing said fluid communication when less than said predetermined gas pressure is in said gas chamber;
disposing water in the reservoir chamber;
connecting the first passage with a source of medical gas, under pressure;
providing a means of administering said gas to the nasal passage of the mammal;
connecting said second passage to said means of administering; and
introducing the medical gas into said first passage;
whereby the medical gas passes through the water and is humidified and thence passes through the second passage, the means for administering and is received by the mammal through the mammal's nasal passages.

2. In an apparatus of the type for moisturizing medical gases having:
(a) a portable housing having an upper portion and a lower portion;
(b) a reservoir chamber within the lower portion of said housing adapted for holding a column of water and having an upper and a lower zone;
(c) a gas chamber within the upper portion of said housing and in gas communication with said reservoir chamber;
(d) a first passage communicating between the lower zone of said reservoir chamber and the outside of said housing, said passage having a first open end in the lower zone of the reservoir chamber and a second open end on the outside of the housing and adapted for connection to a source of said medical gases whereby medical gases may be introduced into the reservoir chamber and moisturized by contact with water held therein; and
(e) a second passage communicating between said gas chamber and the outside of said housing, said second passage having a first open end in said gas chamber and a second open end on the outside of said housing and adapted to connect with a means of delivering moisturized medical gases passed from said gas chamber to a patient in need of receiving said moisturized gases;
wherein the improvement comprises:
(1) a whistle attached to the upper portion of said housing, and which comprises a whistle reed, a nozzle directing gases toward the reed, and a resonating chamber;
(2) a decompression chamber communicating with said nozzle; and (3) valve means between said decompression chamber and said gas chamber, said valve means comprising a valve casing, a valve seat in the bottom of said casing surrounding a valve orifice defining an inlet into the valve casing, said valve orifice opening into said gas chamber, a lightweight poppet adapted to seat in said valve seat under the force of gravity to close the valve orifice and to lift out of said valve seat under a predetermined pressure of gas exerted on the seated poppet through the orifice, and a plurality of relatively narrow bypass channels extending longitudinally through said casing and disposed around said poppet which communicate between said decompression chamber and said valve orifice as soon as said poppet is lifted out of said valve seat, said valve means being adapted to rapidly open fluid communication between said decompression chamber and said gas chamber in response to a predetermined gas pressure in said gas chamber, said valve means closing said fluid communication when less than said predetermined gas pressure is in said gas chamber.

3. Apparatus according to claim 2 wherein said upper portion of said portable housing comprises a removable closure for said housing and said whistle is contained in said closure.

4. Apparatus according to claim 3 wherein the whistle reed of said whistle is an integral part of said closure.

5. Apparatus according to claim 3 wherein the resonating chamber of said whistle is formed in part by the inner walls of said closure.

6. Apparatus according to claim 5 wherein the reed of said whistle forms an angle of 30° with the wall of said closure in which it is positioned and the nozzle of said whistle directs gases toward said reed at an angle of one-half the angle of said reed.

7. Apparatus according to claim 2 wherein said poppet has a lower end for seating on said valve seat, which comprises a first, cone-shaped convex surface which leads from the lowermost point of the lower end upward to a second surface which leads upward on a line parallel with the axis of the weight to a third, annular concave surface.

8. Apparatus according to claim 7 wherein said poppet weighs approximately six grams.

9. Apparatus according to claim 2 wherein said channels are at least two flutes located on opposite sides of said poppet.

* * * * *